(12) United States Patent
Olivera et al.

(10) Patent No.: US 11,083,556 B2
(45) Date of Patent: *Aug. 10, 2021

(54) IMPLANT LOADING DEVICE AND SYSTEM

(71) Applicant: Pulmonx Corporation, Redwood City, CA (US)

(72) Inventors: Ryan Olivera, Granite Bay, CA (US); Hoang Nguyen, San Jose, CA (US)

(73) Assignee: Pulmonx Corporation, Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/436,711

(22) Filed: Jun. 10, 2019

(65) Prior Publication Data

US 2020/0030075 A1 Jan. 30, 2020

Related U.S. Application Data

(63) Continuation of application No. 15/841,898, filed on Dec. 14, 2017, now Pat. No. 10,350,048, which is a continuation of application No. 14/938,216, filed on Nov. 11, 2015, now Pat. No. 9,872,755, which is a continuation of application No. 13/625,615, filed on
(Continued)

(51) Int. Cl.
*A61F 2/95* (2013.01)
*A61F 2/00* (2006.01)
*A61B 17/12* (2006.01)
*A61F 2/04* (2013.01)
(Continued)

(52) U.S. Cl.
CPC ...... *A61F 2/0095* (2013.01); *A61B 17/12031* (2013.01); *A61B 17/12104* (2013.01); *A61B 17/12172* (2013.01); *A61F 2/04* (2013.01); *A61F 2/95* (2013.01); *B65B 1/04* (2013.01); *A61B 2017/0053* (2013.01);
(Continued)

(58) Field of Classification Search
CPC ...................................................... A61F 2/203
USPC ................................................................ 623/9
See application file for complete search history.

(56) References Cited

U.S. PATENT DOCUMENTS 2,981,254 A 4/1961 Vanderbilt
3,657,744 A 4/1972 Robert
(Continued)

FOREIGN PATENT DOCUMENTS

DE 9205797 U1 6/1992
EP 0128433 B1 4/1989
(Continued)

OTHER PUBLICATIONS

Al Jishi et al., "Selective Bronchial Occlusion for Treatment of Bullous Interstitial Emphysema and Bronchopleural Fistula." J. of Pediatric Surgery, 29:1545-1547, 1994.
(Continued)

*Primary Examiner* — Suzette J Gherbi
(74) *Attorney, Agent, or Firm* — Wilson Sonsini Goodrich & Rosati

(57) ABSTRACT

Devices, methods, and systems are provided for loading an implantable device into a container. One aspect of the loading system contains a loader element with a loading tunnel that is configured to gradually contract an implantable device into a compressed state of reduced size relative to an expanded state as the implantable device travels through the loading tunnel.

13 Claims, 9 Drawing Sheets

Related U.S. Application Data

Sep. 24, 2012, now Pat. No. 9,211,181, which is a continuation-in-part of application No. 12/820,393, filed on Jun. 22, 2010, now Pat. No. 8,388,682, which is a continuation of application No. 11/282,940, filed on Nov. 18, 2005, now Pat. No. 7,771,472.

(60) Provisional application No. 61/538,723, filed on Sep. 23, 2011, provisional application No. 60/630,399, filed on Nov. 19, 2004.

(51) Int. Cl.
*B65B 1/04* (2006.01)
*A61B 17/00* (2006.01)

(52) U.S. Cl.
CPC ..... *A61B 2017/1205* (2013.01); *A61F 2/9522* (2020.05); *A61F 2002/043* (2013.01)

(56) References Cited

U.S. PATENT DOCUMENTS

| | | |
|---|---|---|
| 3,667,069 A | 6/1972 | Blackshear et al. |
| 3,788,327 A | 1/1974 | Donowitz |
| 3,874,388 A | 4/1975 | King et al. |
| 4,014,318 A | 3/1977 | Dockum et al. |
| 4,086,665 A | 5/1978 | Poirier |
| 4,212,463 A | 7/1980 | Pratt et al. |
| 4,250,873 A | 2/1981 | Bonnet |
| 4,302,854 A | 12/1981 | Runge |
| 4,477,930 A | 10/1984 | Totten et al. |
| 4,710,192 A | 12/1987 | Liotta et al. |
| 4,732,152 A | 3/1988 | Wallsten et al. |
| 4,759,758 A | 7/1988 | Gabbay |
| 4,774,942 A | 10/1988 | Moellers |
| 4,795,449 A | 1/1989 | Schneider et al. |
| 4,808,183 A | 2/1989 | Panje |
| 4,819,664 A | 4/1989 | Nazari |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,568 A | 8/1989 | Kensey |
| 4,877,025 A | 10/1989 | Hanson |
| 4,879,998 A | 11/1989 | Moellers |
| 4,934,999 A | 6/1990 | Bader |
| 4,968,294 A | 11/1990 | Salama |
| 4,990,151 A | 2/1991 | Wallsten |
| 5,061,274 A | 10/1991 | Kensey |
| 5,116,360 A | 5/1992 | Pinchuk et al. |
| 5,116,564 A | 5/1992 | Jansen et al. |
| 5,123,919 A | 6/1992 | Sauter et al. |
| 5,151,105 A | 9/1992 | Kwan-Gett |
| 5,158,548 A | 10/1992 | Lau et al. |
| 5,161,524 A | 11/1992 | Evans |
| 5,306,234 A | 4/1994 | Johnson |
| 5,352,240 A | 10/1994 | Ross |
| 5,358,518 A | 10/1994 | Camilli |
| 5,366,478 A | 11/1994 | Brinkerhoff et al. |
| 5,382,261 A | 1/1995 | Palmaz |
| 5,392,775 A | 2/1995 | Adkins, Jr. et al. |
| 5,409,019 A | 4/1995 | Wilk |
| 5,411,507 A | 5/1995 | Heckele |
| 5,411,552 A | 5/1995 | Andersen et al. |
| 5,413,599 A | 5/1995 | Imachi et al. |
| 5,417,226 A | 5/1995 | Juma |
| 5,445,626 A | 8/1995 | Gigante |
| 5,453,090 A | 9/1995 | Martinez et al. |
| 5,486,154 A | 1/1996 | Kelleher |
| 5,499,995 A | 3/1996 | Teirstein et al. |
| 5,500,014 A | 3/1996 | Quijano et al. |
| 5,522,881 A | 6/1996 | Lentz |
| 5,562,608 A | 10/1996 | Sekins et al. |
| 5,588,424 A | 12/1996 | Insler et al. |
| 5,645,519 A | 7/1997 | Lee et al. |
| 5,645,565 A | 7/1997 | Rudd et al. |
| 5,649,906 A | 7/1997 | Gory et al. |
| 5,660,175 A | 8/1997 | Dayal |
| 5,662,713 A | 9/1997 | Andersen et al. |
| 5,676,671 A | 10/1997 | Inoue |
| 5,683,451 A | 11/1997 | Lenker et al. |
| 5,697,968 A | 12/1997 | Rogers et al. |
| 5,755,770 A | 5/1998 | Ravenscroft |
| 5,800,339 A | 9/1998 | Salama |
| 5,803,080 A | 9/1998 | Freitag |
| 5,824,037 A | 10/1998 | Fogarty et al. |
| 5,840,081 A | 11/1998 | Andersen et al. |
| 5,843,158 A | 12/1998 | Lenker et al. |
| 5,851,232 A | 12/1998 | Lois |
| 5,855,587 A | 1/1999 | Hyon et al. |
| 5,855,597 A | 1/1999 | Jayaraman |
| 5,855,601 A | 1/1999 | Bessler et al. |
| 5,868,779 A | 2/1999 | Ruiz |
| 5,891,195 A | 4/1999 | Klostermeyer et al. |
| 5,910,144 A | 6/1999 | Hayashi |
| 5,944,738 A | 8/1999 | Amplatz et al. |
| 5,947,997 A | 9/1999 | Pavcnik et al. |
| 5,954,765 A | 9/1999 | Ruiz |
| 5,954,766 A | 9/1999 | Zadno-Azizi et al. |
| 5,957,949 A | 9/1999 | Leonhardt et al. |
| 5,976,174 A | 11/1999 | Ruiz |
| 5,980,455 A | 11/1999 | Daniel et al. |
| 5,984,965 A | 11/1999 | Knapp et al. |
| 5,989,288 A | 11/1999 | Pintauro et al. |
| 6,007,575 A | 12/1999 | Samuels |
| 6,009,614 A | 1/2000 | Morales |
| 6,020,380 A | 2/2000 | Killian |
| 6,022,312 A | 2/2000 | Chaussy et al. |
| 6,024,759 A * | 2/2000 | Nuss ............... A61B 17/68 606/237 |
| 6,027,508 A | 2/2000 | Ren et al. |
| 6,027,525 A | 2/2000 | Suh et al. |
| 6,036,694 A * | 3/2000 | Goble ............... A61F 2/0811 606/304 |
| 6,051,022 A | 4/2000 | Cai et al. |
| 6,068,635 A | 5/2000 | Gianotti |
| 6,068,638 A | 5/2000 | Makower |
| 6,077,291 A | 6/2000 | Das |
| 6,083,255 A | 7/2000 | Laufer et al. |
| 6,123,663 A | 9/2000 | Rebuffat |
| 6,135,729 A | 10/2000 | Aber |
| 6,135,991 A | 10/2000 | Muni et al. |
| 6,141,855 A | 11/2000 | Morales |
| 6,162,245 A | 12/2000 | Jayaraman |
| 6,168,614 B1 | 1/2001 | Andersen et al. |
| 6,174,323 B1 | 1/2001 | Biggs et al. |
| 6,183,520 B1 | 2/2001 | Pintauro et al. |
| 6,190,381 B1 | 2/2001 | Olsen et al. |
| 6,200,333 B1 | 3/2001 | Laufer |
| 6,206,918 B1 | 3/2001 | Campbell et al. |
| 6,232,365 B1 * | 5/2001 | Weiss ............... C08F 20/18 522/178 |
| 6,234,996 B1 | 5/2001 | Bagaoisan et al. |
| 6,240,615 B1 | 6/2001 | Kimes et al. |
| 6,245,102 B1 | 6/2001 | Jayaraman |
| 6,247,471 B1 | 6/2001 | Bower et al. |
| 6,258,100 B1 | 7/2001 | Alferness et al. |
| 6,270,527 B1 | 8/2001 | Campbell et al. |
| 6,280,464 B1 | 8/2001 | Hayashi |
| 6,287,290 B1 | 9/2001 | Perkins et al. |
| 6,287,315 B1 * | 9/2001 | Wijeratne ......... A61B 17/12172 606/108 |
| 6,293,951 B1 | 9/2001 | Alferness et al. |
| 6,302,893 B1 | 10/2001 | Limon et al. |
| 6,312,407 B1 | 11/2001 | Zadno-Azizi et al. |
| 6,325,777 B1 | 12/2001 | Zadno-Azizi et al. |
| 6,325,778 B1 | 12/2001 | Zadno-Azizi et al. |
| 6,327,772 B1 | 12/2001 | Zadno-Azizi et al. |
| 6,328,689 B1 | 12/2001 | Gonzalez et al. |
| 6,355,014 B1 | 3/2002 | Zadno-Azizi et al. |
| 6,398,775 B1 | 6/2002 | Perkins et al. |
| 6,402,754 B1 | 6/2002 | Gonzalez |
| 6,416,554 B1 | 7/2002 | Alferness et al. |
| 6,458,076 B1 | 10/2002 | Pruitt |

(56) References Cited

U.S. PATENT DOCUMENTS

| | | |
|---|---|---|
| 6,485,407 B2 | 11/2002 | Alferness et al. |
| 6,491,706 B1 | 12/2002 | Alferness et al. |
| 6,493,589 B1 | 12/2002 | Medhkour et al. |
| 6,510,846 B1 | 1/2003 | O'Rourke |
| 6,527,761 B1 | 3/2003 | Soltesz et al. |
| 6,558,318 B1 | 5/2003 | Daniel et al. |
| 6,592,594 B2 | 7/2003 | Rimbaugh et al. |
| 6,632,243 B1 | 10/2003 | Zadno-Azizi et al. |
| 6,679,264 B1 | 1/2004 | Deem et al. |
| 6,694,979 B2 | 2/2004 | Deem et al. |
| 6,699,231 B1 | 3/2004 | Sterman et al. |
| 6,837,906 B2 | 1/2005 | Ginn |
| 6,840,243 B2 | 1/2005 | Deem et al. |
| 6,840,957 B2 | 1/2005 | Dimatteo et al. |
| 6,878,141 B1 | 4/2005 | Perkins et al. |
| 6,901,927 B2 | 6/2005 | Deem et al. |
| 6,904,909 B2 | 6/2005 | Deem et al. |
| 6,905,518 B2 | 6/2005 | Ginn |
| 6,941,950 B2 | 9/2005 | Wilson et al. |
| 7,011,094 B2 | 3/2006 | Rapacki et al. |
| 7,399,315 B2 | 7/2008 | Lobbi et al. |
| 7,771,472 B2* | 8/2010 | Hendricksen .... A61B 17/12104 623/9 |
| 7,854,228 B2* | 12/2010 | Wilson .................. A61F 2/2412 128/205.24 |
| 8,673,020 B2* | 3/2014 | Sobrino-Serrano ........................ A61F 2/2412 623/23.68 |
| 9,211,181 B2* | 12/2015 | Olivera ...................... A61F 2/04 |
| 9,872,755 B2* | 1/2018 | Olivera ...................... A61F 2/04 |
| 10,350,048 B2* | 7/2019 | Olivera ............ A61B 17/12172 |
| 2001/0025132 A1 | 9/2001 | Alferness et al. |
| 2001/0037808 A1 | 11/2001 | Deem et al. |
| 2001/0041906 A1 | 11/2001 | Gonzalez |
| 2001/0051799 A1 | 12/2001 | Ingenito |
| 2001/0052344 A1 | 12/2001 | Doshi |
| 2001/0056274 A1 | 12/2001 | Perkins et al. |
| 2002/0007831 A1 | 1/2002 | Davenport et al. |
| 2002/0026233 A1 | 2/2002 | Shaknovich |
| 2002/0062120 A1 | 5/2002 | Perkins et al. |
| 2002/0077593 A1 | 6/2002 | Perkins et al. |
| 2002/0077696 A1 | 6/2002 | Zadno-Azizi et al. |
| 2002/0087153 A1 | 7/2002 | Roschak et al. |
| 2002/0095209 A1 | 7/2002 | Zadno-Azizi et al. |
| 2002/0111619 A1 | 8/2002 | Keast et al. |
| 2002/0111620 A1 | 8/2002 | Cooper et al. |
| 2002/0112729 A1 | 8/2002 | Devore et al. |
| 2002/0138135 A1 | 9/2002 | Duerig et al. |
| 2003/0018327 A1 | 1/2003 | Truckai et al. |
| 2003/0018344 A1 | 1/2003 | Kaji et al. |
| 2003/0050648 A1 | 3/2003 | Alferness et al. |
| 2003/0070682 A1 | 4/2003 | Wilson et al. |
| 2003/0070683 A1 | 4/2003 | Deem et al. |
| 2003/0075169 A1 | 4/2003 | Deem et al. |
| 2003/0075170 A1 | 4/2003 | Deem et al. |
| 2003/0083671 A1 | 5/2003 | Rimbaugh et al. |
| 2003/0127090 A1 | 7/2003 | Gifford et al. |
| 2003/0164168 A1 | 9/2003 | Shaw |
| 2003/0192550 A1 | 10/2003 | Deem et al. |
| 2003/0192551 A1 | 10/2003 | Deem et al. |
| 2003/0199972 A1 | 10/2003 | Zadno-Azizi et al. |
| 2003/0212452 A1 | 11/2003 | Zadno-Azizi et al. |
| 2003/0228344 A1 | 12/2003 | Fields et al. |
| 2004/0016435 A1 | 1/2004 | Deem et al. |
| 2004/0039250 A1 | 2/2004 | Tholfsen et al. |
| 2004/0055606 A1 | 3/2004 | Hendricksen et al. |
| 2004/0060563 A1 | 4/2004 | Rapacki et al. |
| 2004/0074491 A1 | 4/2004 | Hendricksen et al. |
| 2004/0089306 A1 | 5/2004 | Hundertmark et al. |
| 2004/0134487 A1 | 7/2004 | Deem et al. |
| 2004/0148035 A1 | 7/2004 | Barrett et al. |
| 2004/0154621 A1 | 8/2004 | Deem et al. |
| 2004/0194780 A1 | 10/2004 | Doshi |
| 2004/0200484 A1 | 10/2004 | Springmeyer |
| 2004/0211434 A1 | 10/2004 | Loomas et al. |
| 2005/0005936 A1 | 1/2005 | Wondka |
| 2005/0015106 A1 | 1/2005 | Perkins et al. |
| 2005/0016530 A1 | 1/2005 | McCutcheon et al. |
| 2005/0022809 A1 | 2/2005 | Wondka |
| 2005/0033310 A1 | 2/2005 | Alferness et al. |
| 2005/0033344 A1 | 2/2005 | Dillard et al. |
| 2005/0051163 A1 | 3/2005 | Deem et al. |
| 2005/0061322 A1 | 3/2005 | Freitag |
| 2005/0066974 A1 | 3/2005 | Fields et al. |
| 2005/0087137 A1 | 4/2005 | Park et al. |
| 2005/0125076 A1 | 6/2005 | Ginn |
| 2005/0137714 A1 | 6/2005 | Gonzalez et al. |
| 2005/0145253 A1 | 7/2005 | Wilson et al. |
| 2005/0161048 A1 | 7/2005 | Rapacki et al. |
| 2005/0166925 A1 | 8/2005 | Wilson et al. |
| 2005/0171396 A1 | 8/2005 | Pankratov et al. |
| 2005/0178389 A1 | 8/2005 | Shaw et al. |
| 2005/0196344 A1 | 9/2005 | McCutcheon et al. |
| 2005/0203483 A1 | 9/2005 | Perkins et al. |
| 2006/0004305 A1 | 1/2006 | George et al. |
| 2006/0020347 A1 | 1/2006 | Barrett et al. |
| 2006/0030863 A1 | 2/2006 | Fields et al. |
| 2006/0162731 A1 | 7/2006 | Wondka et al. |
| 2008/0072914 A1 | 3/2008 | Hendricksen et al. |
| 2008/0091166 A1 | 4/2008 | Fitzgerald et al. |
| 2008/0200896 A1 | 8/2008 | Shmulewitz et al. |
| 2008/0221703 A1 | 9/2008 | Que et al. |
| 2008/0269878 A1 | 10/2008 | Iobbi |
| 2008/0281350 A1* | 11/2008 | Sepetka ........... A61B 17/12172 606/200 |
| 2010/0030256 A1* | 2/2010 | Dubrul ............. A61B 17/12022 606/200 |
| 2010/0292779 A1 | 11/2010 | Straubinger et al. |
| 2010/0319708 A1* | 12/2010 | Mahr ........................ A61F 2/82 128/848 |
| 2011/0010910 A1 | 1/2011 | Hendricksen et al. |
| 2011/0022149 A1* | 1/2011 | Cox ................ A61B 17/12181 623/1.11 |
| 2011/0046712 A1 | 2/2011 | Melsheimer et al. |
| 2011/0130834 A1* | 6/2011 | Wilson .................. A61F 2/2412 623/9 |
| 2011/0166593 A1* | 7/2011 | Paul, Jr. ........... A61B 17/12172 606/200 |
| 2011/0270410 A1* | 11/2011 | Stack .................... A61F 5/0036 623/23.65 |
| 2013/0204309 A1* | 8/2013 | Hoof ..................... A61B 17/864 606/304 |
| 2015/0094809 A1* | 4/2015 | Perrin ...................... A61F 2/04 623/9 |

FOREIGN PATENT DOCUMENTS

| | | |
|---|---|---|
| EP | 0621015 A1 | 10/1994 |
| EP | 1078601 A2 | 2/2001 |
| EP | 1151729 A1 | 11/2001 |
| EP | 1078601 A3 | 5/2002 |
| GB | 2324729 A | 11/1998 |
| RU | 2140211 C1 | 10/1999 |
| SU | 852321 A1 | 8/1981 |
| SU | 1371700 A1 | 2/1988 |
| SU | 1593651 A1 | 9/1990 |
| WO | WO-9426175 A1 | 11/1994 |
| WO | WO-9532018 A1 | 11/1995 |
| WO | WO-9634582 A1 | 11/1996 |
| WO | WO-9639960 A1 | 12/1996 |
| WO | WO-9744085 A2 | 11/1997 |
| WO | WO-9800840 A1 | 1/1998 |
| WO | WO-9814120 A1 | 4/1998 |
| WO | WO-9819633 A1 | 5/1998 |
| WO | WO-9744085 A3 | 9/1998 |
| WO | WO-9839047 A1 | 9/1998 |
| WO | WO-9844854 A1 | 10/1998 |
| WO | WO-9848706 A1 | 11/1998 |
| WO | WO-9901076 A1 | 1/1999 |
| WO | WO-9913801 A1 | 3/1999 |
| WO | WO-9926692 A1 | 6/1999 |
| WO | WO-9932040 A1 | 7/1999 |
| WO | WO-9942059 A2 | 8/1999 |

(56) References Cited

FOREIGN PATENT DOCUMENTS

| | | |
|---|---|---|
| WO | WO-9942161 A2 | 8/1999 |
| WO | WO-9942161 A3 | 10/1999 |
| WO | WO-9942059 A3 | 11/1999 |
| WO | WO-9964109 A1 | 12/1999 |
| WO | WO-0015149 A1 | 3/2000 |
| WO | WO-0042950 A2 | 7/2000 |
| WO | WO-0051510 A1 | 9/2000 |
| WO | WO-0062699 A2 | 10/2000 |
| WO | WO-0042950 A3 | 11/2000 |
| WO | WO-0078386 A1 | 12/2000 |
| WO | WO-0078407 A1 | 12/2000 |
| WO | WO-0102042 A1 | 1/2001 |
| WO | WO-0103642 A1 | 1/2001 |
| WO | WO-0105334 A1 | 1/2001 |
| WO | WO-0110313 A1 | 2/2001 |
| WO | WO-0110314 A2 | 2/2001 |
| WO | WO-0112104 A1 | 2/2001 |
| WO | WO-0113839 A1 | 3/2001 |
| WO | WO-0113908 A2 | 3/2001 |
| WO | WO-0062699 A3 | 4/2001 |
| WO | WO-0145590 A2 | 6/2001 |
| WO | WO-0149213 A2 | 7/2001 |
| WO | WO-0154585 A1 | 8/2001 |
| WO | WO-0154625 A1 | 8/2001 |
| WO | WO-0154685 A1 | 8/2001 |
| WO | WO-0166190 A2 | 9/2001 |
| WO | WO-0174271 A1 | 10/2001 |
| WO | WO-0187170 A1 | 11/2001 |
| WO | WO-0189366 A2 | 11/2001 |
| WO | WO-0195786 A2 | 12/2001 |
| WO | WO-0113908 A3 | 1/2002 |
| WO | WO-0149213 A3 | 1/2002 |
| WO | WO-0205884 A2 | 1/2002 |
| WO | WO-0145590 A3 | 3/2002 |
| WO | WO-0222072 A2 | 3/2002 |
| WO | WO-0195786 A3 | 4/2002 |
| WO | WO-0232333 A1 | 4/2002 |
| WO | WO-0234322 A2 | 5/2002 |
| WO | WO-0238038 A2 | 5/2002 |
| WO | WO-0247575 A2 | 6/2002 |
| WO | WO-02056794 A2 | 7/2002 |
| WO | WO-02064045 A1 | 8/2002 |
| WO | WO-02064190 A2 | 8/2002 |
| WO | WO-02069823 A2 | 9/2002 |
| WO | WO-02064190 A3 | 10/2002 |
| WO | WO-02056794 A3 | 11/2002 |
| WO | WO-02069823 A3 | 11/2002 |
| WO | WO-02094087 A1 | 11/2002 |
| WO | WO-0247575 A3 | 12/2002 |
| WO | WO-0234322 A3 | 1/2003 |
| WO | WO-03022124 A2 | 3/2003 |
| WO | WO-03030975 A2 | 4/2003 |
| WO | WO-0238038 A3 | 5/2003 |
| WO | WO-03041779 A1 | 5/2003 |
| WO | WO-0166190 A3 | 8/2003 |
| WO | WO-0222072 A3 | 8/2003 |
| WO | WO-03022124 A3 | 8/2003 |
| WO | WO-03030975 A3 | 8/2003 |
| WO | WO-03075796 A2 | 9/2003 |
| WO | WO-03099164 A1 | 12/2003 |
| WO | WO-2004006767 A2 | 1/2004 |
| WO | WO-2004010845 A2 | 2/2004 |
| WO | WO-2004010845 A3 | 6/2004 |
| WO | WO-2004049974 A2 | 6/2004 |
| WO | WO-2004049974 A3 | 8/2004 |
| WO | WO-2004080347 A2 | 9/2004 |
| WO | WO-2005000161 A2 | 1/2005 |
| WO | WO-2005006957 A2 | 1/2005 |
| WO | WO-2005007023 A2 | 1/2005 |
| WO | WO-2005013808 A2 | 2/2005 |
| WO | WO-2005013835 A1 | 2/2005 |
| WO | WO-2005007023 A3 | 5/2005 |
| WO | WO-2004080347 A3 | 6/2005 |
| WO | WO-2005006957 A3 | 7/2005 |
| WO | WO-2005013808 A3 | 8/2005 |
| WO | WO-2005087137 A1 | 9/2005 |
| WO | WO-2005000161 A3 | 10/2005 |
| WO | WO-2004006767 A3 | 12/2007 |
| WO | WO-0189366 A3 | 6/2009 |

OTHER PUBLICATIONS

Autocath.RTM. 100—Nonsurgical, Intraurethral Bladder Control Device for Incontinent and Retentive Women—Dr. Kulisz's Development, retrieved from the Internet<http://www.kulisz.com/autocath.htm> on Oct. 22, 2009.
Derwent# 007607249 WPI Acc. No. 1988-241181/198834 (citing Russian Application No. SU4026409, published Feb. 21, 1986.) Russian Patent No. SU 1371700.
Derwent# 008650867 WPI Acc. No. 1991-154896/199121 (citing Russian Application No. SU4280143, published Jul. 7, 1987), Russian Patent No. SU 1593651.
Derwent citing Russian Patent No. RU 2140211, published Oct. 27, 1999, for: "Method of surgical treatment of patients with pathology of respiratory organs complicated with pulmonary hemorrhages".
Derwent citing Soviet Union Patent No. SU 852-321, published Jul. 8, 1981, for: Treatment for acute pulmonary and pleural disease in children —by pneumo-abcessotomy simultaneous with occlusion of affected lung part.
"European search report and opinion dated May 19, 2015 for EP Application No. 12834340.7.".
Harris et al., "The Experimental Production in Dogs of Emphysema with Associated Asthmatic Syndrome by Means of an Intratracheal Ball Valve," J. Lab. Clini. Med., 1919; 9(iv):75-88.
International search report and written opinion dated Feb. 27, 2013 for PCT/US2012/056968.
Lewis et al., "Pulmonary Interstitial Emphysema: Selective Broncial Occlusion with a Swan-Ganz Catheter", Archives of Disease in Childhood, 1988; 63:313-315.
Mathew et al., "Selective bronchial obstruction for treatment of bullous interstitial emphysema." J. of Ped., 96:475-477, 1980.
"Notice of allowance dated May 13, 2010 for U.S. Appl. No. 11/282,940.".
"Notice of allowance dated Aug. 12, 2015 for U.S. Appl. No. 13/625,615.".
Notice of Allowance dated Sep. 15, 2017 for U.S. Appl. No. 14/938,216.
"Notice of allowance dated Nov. 2, 2012 for U.S. Appl. No. 12/820,393.".
Office Action dated Mar. 30, 2017 for U.S. Appl. No. 14/938,216.
Office action dated May 17, 2012 for U.S. Appl. No. 12/820,393.
Office action dated Sep. 27, 2018 for U.S. Appl. No. 15/841,898.
Okada et al., "Emergent Bronchofiberoptic Bronchial Occlusion for Intractable Pneumothorax with Severe Emphysema", Jpn J Thorac Cardiovasc Surg. Nov. 1998;46(11):1078-81.
Puhakka et al., "Acute Bronchial Obstruction: An Experimental Rabbit Model Study", Int. J. of Pediatric Otorhinolaryngology, 18:107-118, 1989.
Snider et al., "The Definition of Emphysema: Report of the National Heart Lung and Blood Institute, Division of Lung Diseases Workshop," Am. Rev. Respir. Dis. 1985; 132:182-185.
U.S. Appl. No. 13/625,615, filed Sep. 24, 2012.
U.S. Appl. No. 15/841,898 Office Action dated Feb. 22, 2018.
Woodring et al., "Pneumothorax ex Vacuo", Chest, 100:1102-1124, 1996.

* cited by examiner

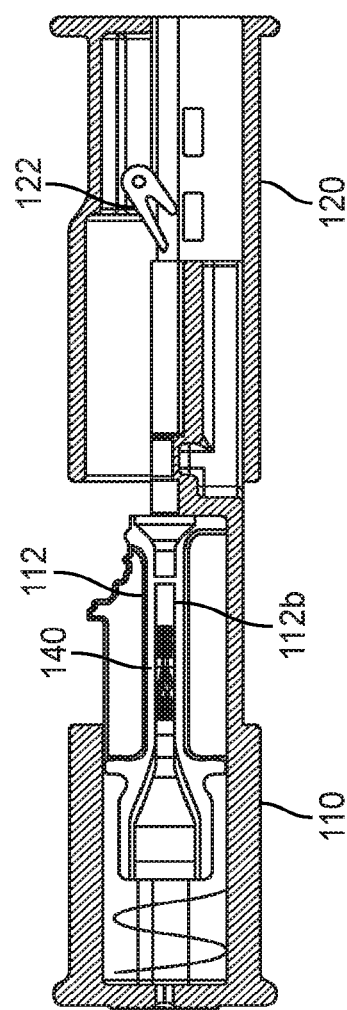
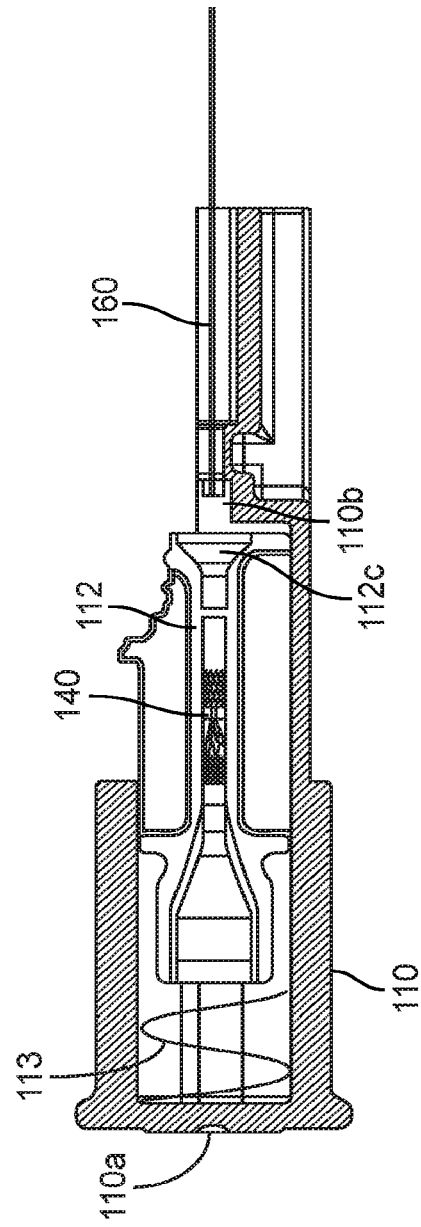
FIG. 4A
FIG. 4B

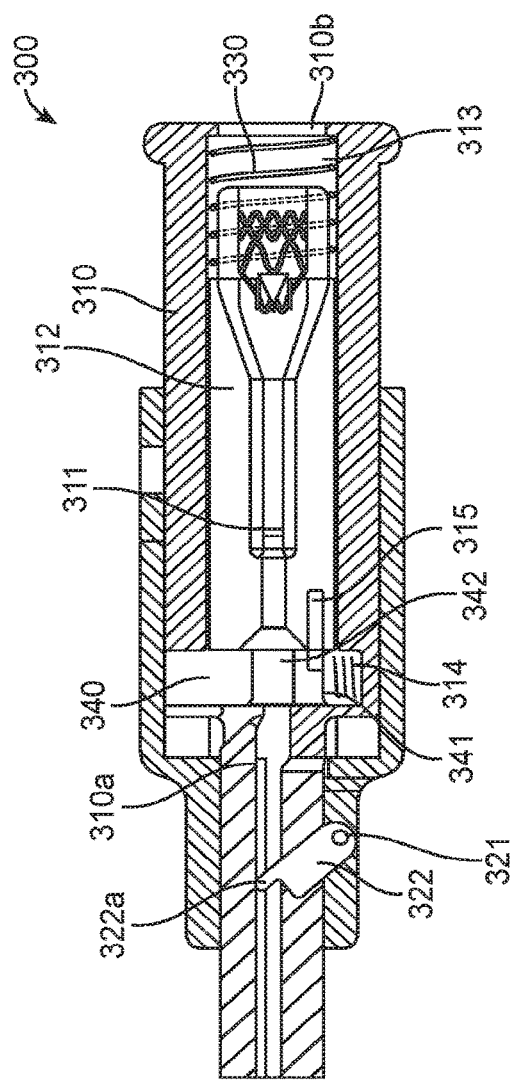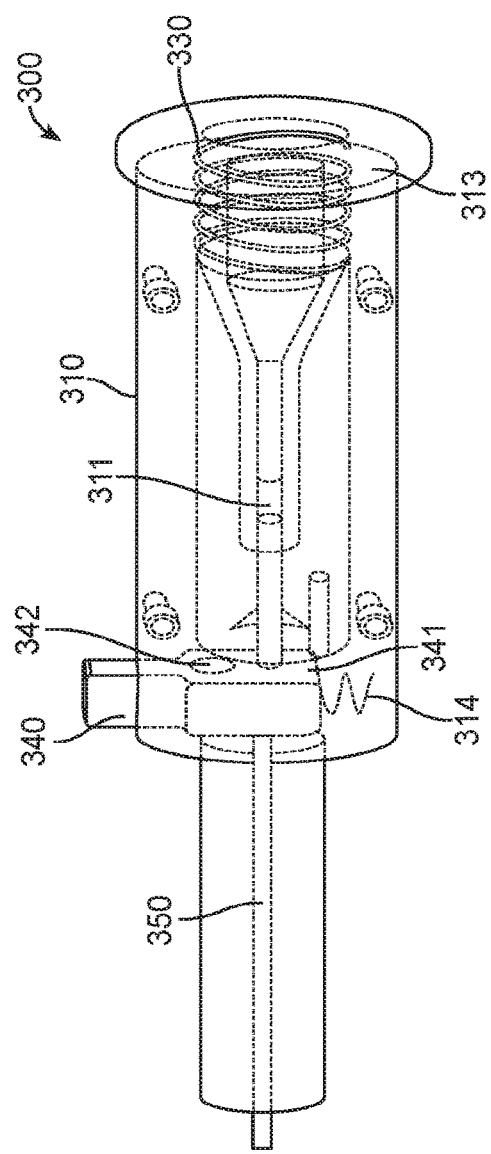
FIG. 5A
FIG. 5B

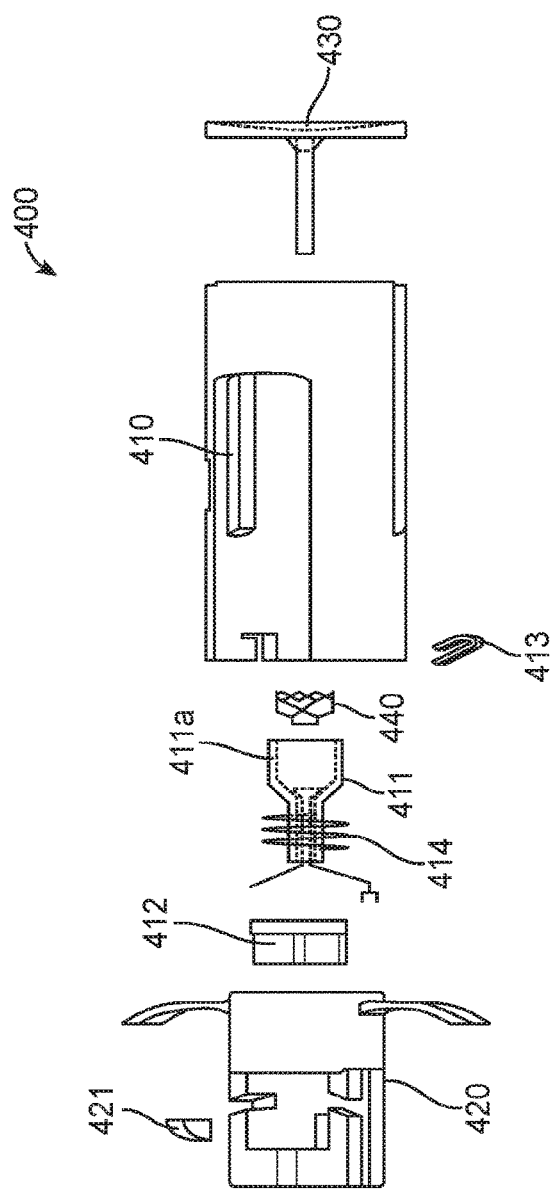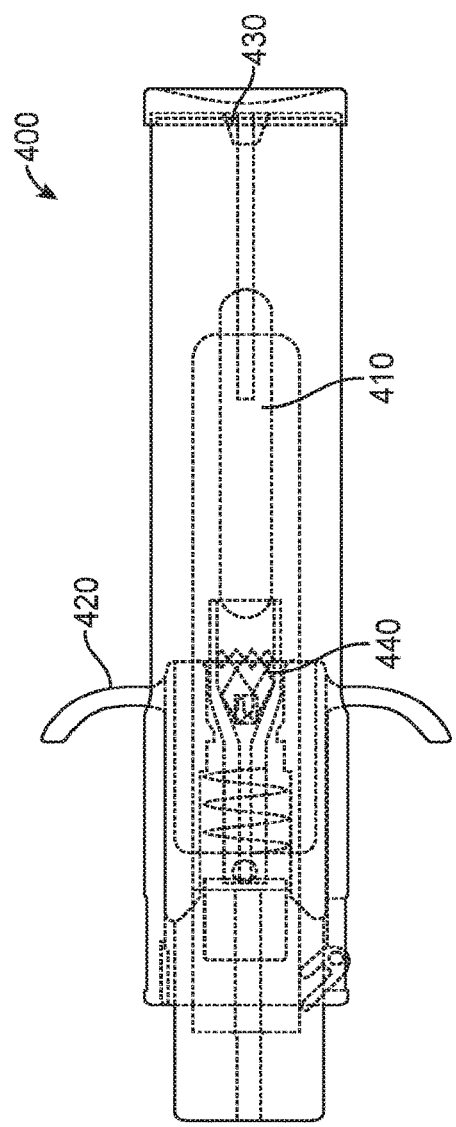

IMPLANT LOADING DEVICE AND SYSTEM

CROSS-REFERENCES TO RELATED APPLICATIONS

This application is a continuation of U.S. patent application Ser. No. 15/841,898, filed Dec. 14, 2017, now U.S. Pat. No. 10,350,048, which is a continuation of U.S. patent application Ser. No. 14/938,216, filed Nov. 11, 2015, now U.S. Pat. No. 9,872,755, which is a continuation of U.S. patent application Ser. No. 13/625,615, filed Sep. 24, 2012, now U.S. Pat. No. 9,211,181, which claims the benefit of Provisional Application No. 61/538,723, filed Sep. 23, 2011, the full disclosure of which is incorporated herein by reference; U.S. patent application Ser. No. 13/625,615, filed Sep. 24, 2012, now U.S. Pat. No. 9,211,181, is also a continuation-in-part application of U.S. patent application Ser. No. 12/820,393, filed on Jun. 22, 2010, now U.S. Pat. No. 8,388,682, which is a continuation of U.S. patent application Ser. No. 11/282,940, filed Nov. 18, 2005, now U.S. Pat. No. 7,771,472, which claims the benefit and priority of U.S. Provisional Application No. 60/630,399, filed on Nov. 19, 2004, all of which are incorporated herein by reference.

FIELD OF THE INVENTION

Present embodiments relate generally to devices, methods, and systems for loading an implantable device into a container.

DESCRIPTION OF THE RELATED ART

Pulmonary diseases, such as chronic obstructive pulmonary disease, (COPD), reduce the ability of one or both lungs to fully expel air during the exhalation phase of the breathing cycle. Such diseases are accompanied by chronic or recurrent obstruction to air flow within the lung. Because of the increase in environmental pollutants, cigarette smoking, and other noxious exposures, the incidence of COPD has increased dramatically in the last few decades and now ranks as a major cause of activity-restricting or bed-confining disability in the United States. COPD can include such disorders as chronic bronchitis, bronchiectasis, asthma, and emphysema.

It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung. The reduced air volume exerts less force on the airway, which allows the airway to close before all air has been expelled, another factor that prevents full exhalation.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Some recent treatments include the use of devices that isolate a diseased region of the lung in order to reduce the volume of the diseased region, such as by collapsing the diseased lung region. According to such treatments, a delivery catheter is used to implant one or more implantable devices in airways feeding a diseased region of the lung to regulate fluid flow to the diseased lung region in order to fluidly isolate the region of the lung. These implanted implantable devices can be, for example, one-way valves that allow flow in the exhalation direction only, occluders or plugs that prevent flow in either direction, or two-way valves that control flow in both directions.

The implantable device is radially compressed into a contracted size for loading into the delivery catheter or a container associated with the catheter. It can be difficult to properly compress the implantable device to a size small enough to fit in the delivery catheter. Thus, there is a need for devices for properly compressing and loading an implantable device into a container.

SUMMARY

Present disclosure relates to aspects of devices, methods, and systems for loading an implantable device into a container.

In one aspect, an embodiment of a loading system comprises a loader element with a loading tunnel that is configured to gradually contract an implantable device into a compressed state of reduced size relative to an expanded state as the implantable device travels through the loading tunnel. The loading system further comprises a puller element that is removably attached to the implantable device via a suture, wherein the puller element pulls the implantable device through the loading tunnel. In one aspect, the puller element automatically releases the suture after the implantable device contracts into the compressed state.

In one aspect, a loading system further comprises a rotator that is disposed on the puller element that is configured to be removably attached to a portion of the suture, wherein a rotation of the rotator causes the suture to detach from the rotator. In another aspect, the rotator may be disposed on the loader element.

In another aspect, the loading system further comprises a plunger element, wherein the plunger element comprises an elongated portion that is configured to push the implantable device through the loading tunnel. In one aspect, the plunger element is configured to push the implantable device into a delivery catheter.

In another aspect, the loading tunnel of the loading system comprises a funnel housing that defines an internal, funnel-shaped loading cavity.

In yet another aspect, the loading tunnel of the loading system further defines an internal transfer cavity that communicates with the loading cavity. In one aspect, the transfer cavity is sized to receive the implantable device from the loading cavity and retain the implantable device in the compressed state.

In yet another aspect, the loading tunnel of the loading system further defines a container cavity that communicates with the transfer cavity. In one aspect, the container cavity is sized to receive a container that receives the implantable device in the compressed state.

In one aspect, the implantable device is a pulmonary implant that is configured to be placed within a lung region. In another aspect, the container is a housing of a delivery catheter that is configured to receive the compressed implantable device.

In yet another aspect, an embodiment of the loading system further comprises a tension element that is configured to communicate a force to the loading tunnel. Additionally or optionally, an aspect of the loading system comprises a container locking element that is configured to secure and align the container with the loader element.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

FIGS. 4A-4C show various steps of an exemplary operation of one embodiment of the loading system;

FIGS. 5A-5B illustrate an embodiment of the loading system comprising a catheter locking element;

FIGS. 6A-6C illustrate an alternative embodiment of the loading system.

DETAILED DESCRIPTION

Figure 1A:
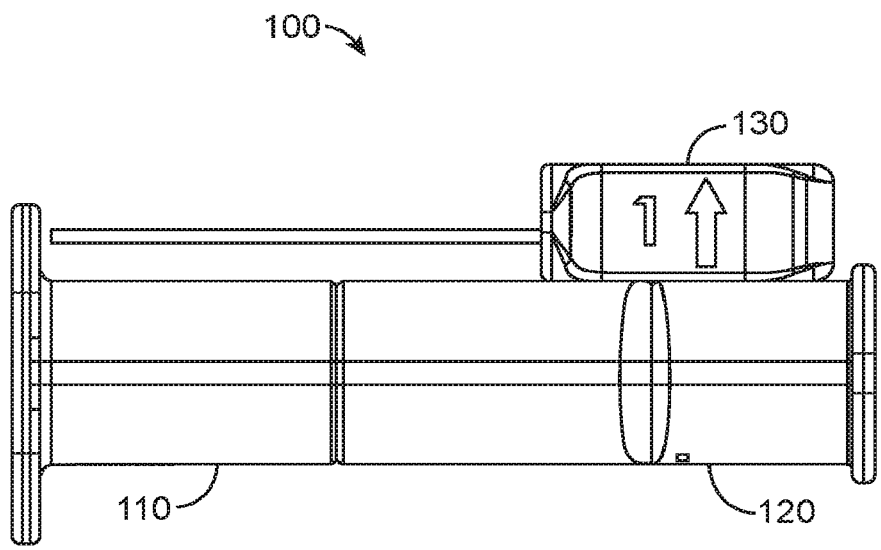
FIG. 1A shows one embodiment of a loading system where various elements of the loading system are connected.

Although the detailed description contains many specifics, these should not be construed as limiting the scope of the disclosure but merely as illustrating different examples and aspects of the disclosure. It should be appreciated that the scope of the disclosure includes other embodiments not discussed herein. Various other modifications, changes and variations which will be apparent to those skilled in the art may be made in the arrangement, operation and details of the method, device, and system of the present embodiments disclosed herein without departing from the spirit and scope of the disclosure as described here.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Disclosed herein are methods, devices and systems for loading an implantable device into a delivery device for delivering the apparatus to a body region, such as a bronchial passageway.

Throughout this disclosure, reference is made to the term "implantable device". As used herein, the term "implantable device" refers to various collapsible and/or self-expanding implant including implants configured to maintain openings in vascular, urinary, biliary, esophageal, and renal tracts, and vena cava filters. Furthermore, it is contemplated that the implantable device may be various pulmonary implants configured to be placed within a lung region to treat pulmonary disorders including but limited to flow restrictive devices such as valves including one-way valves that allow flow in the exhalation direction only, occluders or plugs that prevent flow in either direction, or two-way valves that control flow in both directions.

In one embodiment, present disclosure describes devices, systems, and methods for loading a collapsible pulmonary implant into a delivery system, such as a delivery catheter, in preparation for delivering the implant into a lung region such as the pulmonary airways of a patient. In one embodiment, collapsible pulmonary implants are made of memory-shape materials, such as Nitinol, and are compressed to enable delivery through relatively small and curved bodily pathways to the lung region. In one embodiment, delivery devices, such as catheters, retain the collapsed pulmonary implants in a radially compressed state for delivery to the treatment site, where the implant is released into the lung region and regains its non-compressed shape. The present embodiments disclose various aspects of loading devices that collapse such implants and optionally insert them into a container such as a delivery catheter.

Figure 1B:
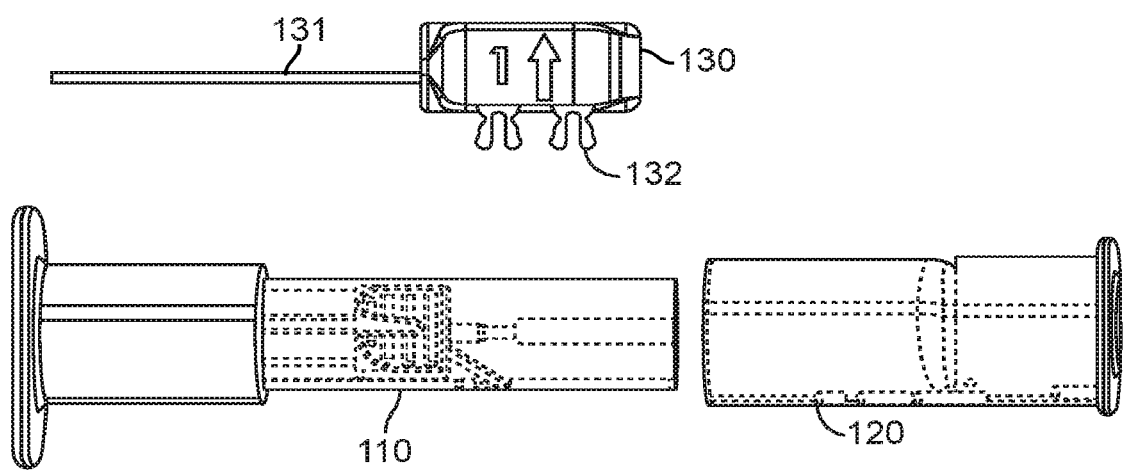
FIG. 1B shows one embodiment of a loading system where the various elements are separated.

FIGS. 1A and 1B show two perspective views of one embodiment of a loading system 100 for compressing an implantable device such as a pulmonary implant and optionally for inserting the implantable device into a housing of a delivery catheter. As seen in FIGS. 1A and 1B, one embodiment of the loading system 100 comprises a loader element 110, a puller element 120, and a plunger element 130. The plunger element 130 comprises an elongated portion 131 and optionally comprises a locking element 132 whereby the locking element 132 is configured to be inserted into the loader element 110 and the puller element 120 such that the loading system 100 may be configured, at least before the loading operation, as an inter-connected discrete unit. Alternatively, the loader element 110 and the puller element 120 may be secured through other locking or securing means and the plunger element 130 may be a separate unit.

Referring now to FIGS. 2A-2D, where various components of one embodiment of the loader element 110 and the puller element 120 are shown. As described in detail below, the loader element 110 is used to compress a collapsible implantable device 140 to a size that can fit into a container, such as a housing of the delivery catheter. Additionally and optionally the loader element 110 is configured to facilitate the alignment of the compressed implantable device 140 with a container, such as a housing of the delivery catheter. As seen in FIG. 2, the loader element 110 comprises a loading tunnel 112 disposed longitudinally within the loader housing 111. In one embodiment, the loading tunnel 112 may comprise three regions, including a funnel-shaped loading region 112a, a container region 112b, and a catheter region 112c. The loading region 112a of the loading tunnel 112 gradually reduces in diameter moving in a rearward direction from the front opening 110a toward the rear opening 110b of the loader element 110 so as to provide the loading region 112a with a funnel shape. The housing region 112b has a shape that substantially conforms to the outer shape of the catheter housing or configured to receive a portion of the catheter so that the catheter housing may be inserted into and/or aligned with the housing region 112c. The catheter region 112c is shaped to receive the housing of the delivery catheter. Additionally and optionally, the loading tunnel 112 may be connected to a tension element 113 exemplarily shown as a spring that is configured to apply a force to the loading tunnel towards the front opening 110a.

Figure 2A:
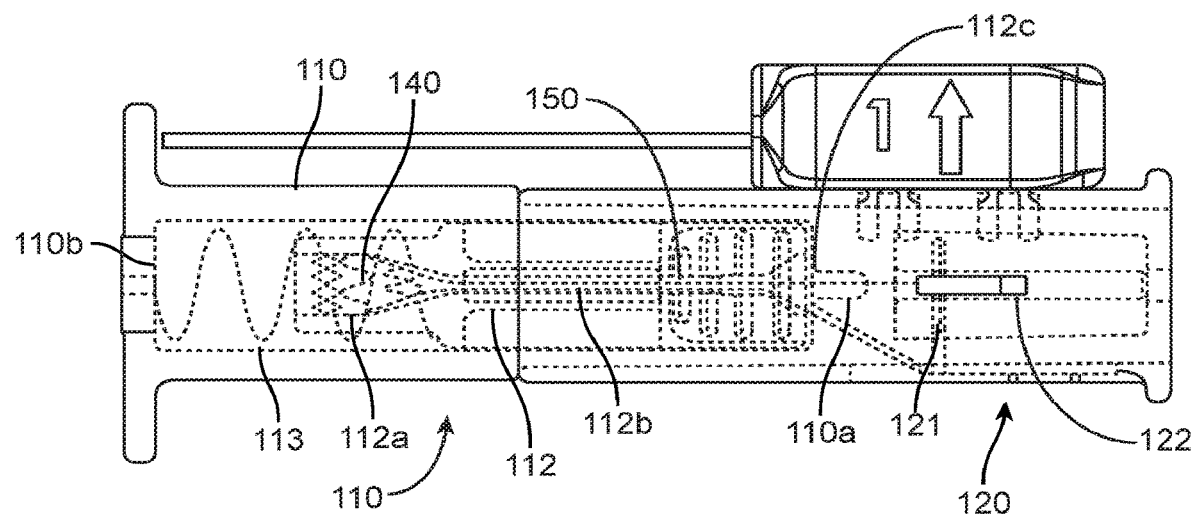
FIGS. 2A-2B show two different views of the various components of one embodiment of the loader element and the puller element.
Figure 2B:
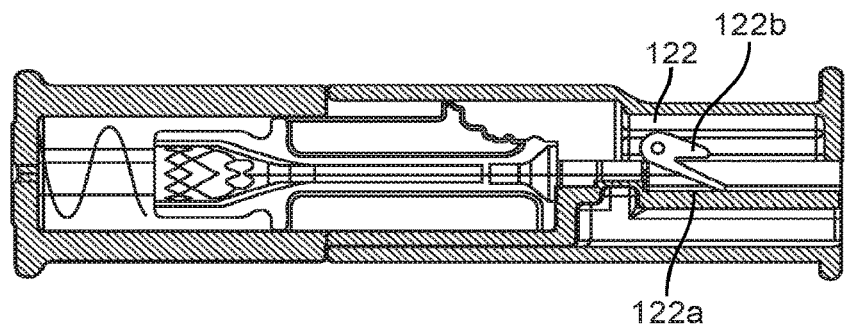

Referring now to the puller element 120, which in one embodiment may comprise a substantially cylindrical hollow body. The puller element 120 comprises a pin 121 disposed on the hollow body or it may be suspended within the hollow body. The puller element 120 further comprises a moveable rotator 122 that is configured to rotate along the pin 121. As seen in FIG. 2B, in one embodiment, the rotator 122 may comprise a body that is configured to connect to the pin 121, a first tine 122a and a second tine 122b, whereby the first tine 122a is longer than the second tine 122b. In one embodiment, one or both tines may be substantially triangular in shape such that the base of the tines that is connected to the body of the rotator is larger than the tip of the tines. Alternatively, the tines may assume various other configurations. Furthermore, it is contemplated that the rotator may comprise a single tine.

The loader element 110 further comprises a rotator track that is configured to accommodate the rotator 122. The rotator 122 is received by the tack disposed on the loader element 110 such that the rotator 122 resides within the rotator track when the loader element 110 and the puller element 120 are connected. The rotator track is further configured to allow the rotator 122 to slide along the rotator track during the loading operation, when the puller element 120 is moved away from the loader element 110.

Figure 2C:
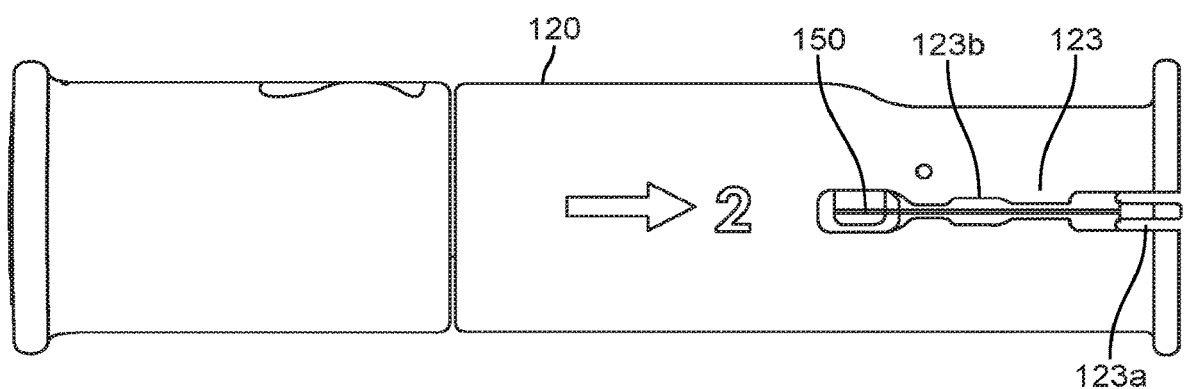
FIG. 2C shows one embodiment of a suture attachment element disposed on the puller element.

As seen in FIG. 2C, the loading system 100 further comprises at least one flexible element that is configured to connect the puller element 120 and the implantable device 140. The flexible element may be a wire or suture, such as polypropylene monofilament suture. In one embodiment, the suture 150 is affixed to the puller element 120 by one or more adhesives configured to bond the suture 150 to the puller element 120. Alternatively or additionally, the second end of the suture 150 may be affixed to the puller element 120 by fastening, tying, or looping the suture 150 to the puller element 120. It is contemplated that the puller element 120 comprises a suture attachment element 123 that is configured to receive the second portion of the suture 150 and enables and/or facilitates affixing the suture 130 to the puller element 120. In one embodiment, the suture attachment element 123 may comprise an attachment anchor 123a where the suture 150 may be attached to the attachment anchor 123a by fastening, tying, and/or looping around the attachment anchor 123a. The attachment element 123 may further comprise a receiving track configured to receive the suture 150 and may comprise slots where adhesives may be applied to affix the suture 150 to the puller element 120.

In one embodiment, the suture 150 is configured as a suture loop that is removably attached to the implantable device 140 by threading the loop through a portion of the implantable device 140 as described in co-pending U.S. application Ser. No. 12/820,393. The suture loop is further removably attached to the rotator 122 such that the suture loop resides between the first and second tines of the rotator 122.

Figure 3:
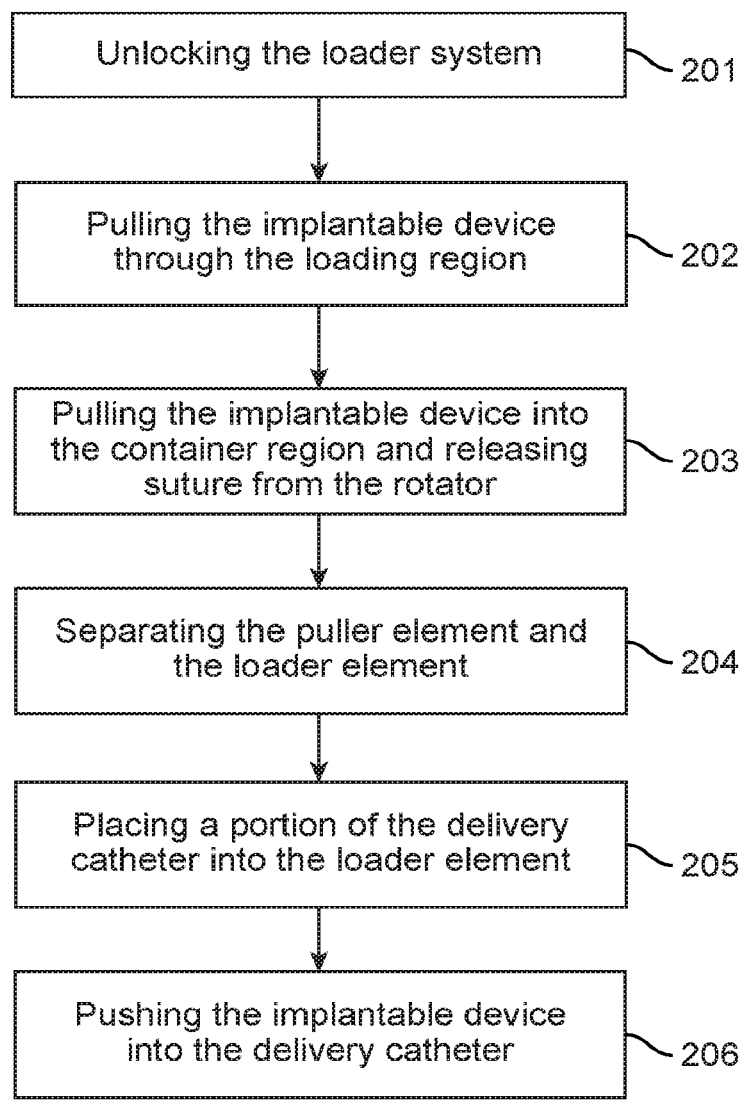
FIG. 3 is a flow diagram illustrating an exemplary operation of one embodiment of the loading system.
Figure 4C:
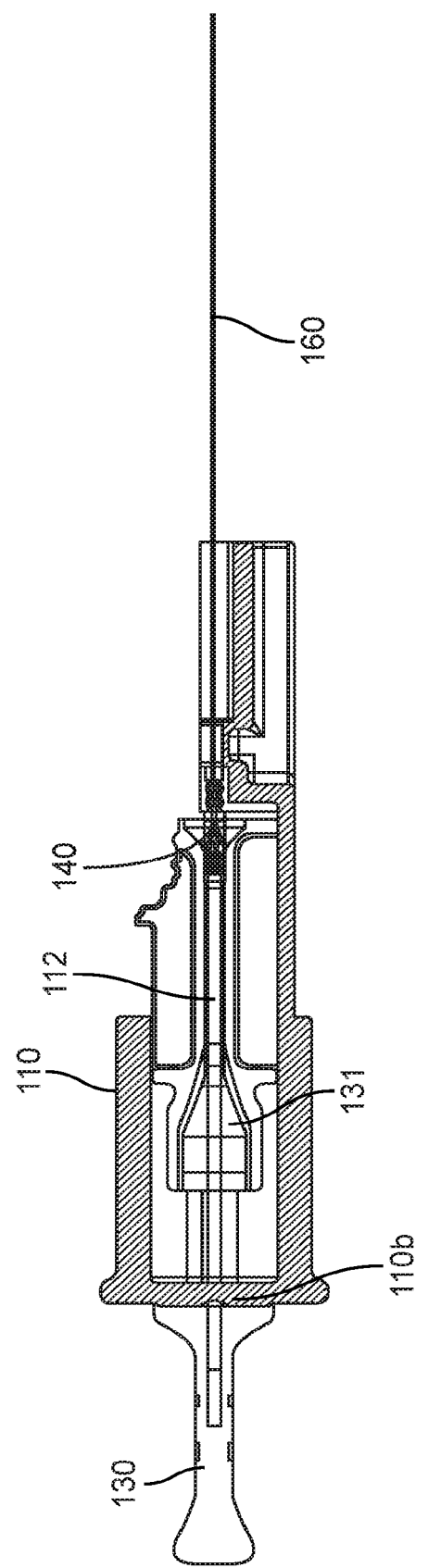

Referring now to FIG. 3, which is a flow diagram that illustrates exemplary steps of operating one embodiment of the loading system. Aspects of the steps described herein are also illustrated in FIGS. 4A-4C as well as FIGS. 1A-1B. In one embodiment, as seen in FIG. 1A, the loading system 100 comprising a loader element 110, a pulling element 120, and a plunger element 130 are mated to form a discrete unit. It is further noted that the implantable device 140 is placed within loading region 112a of the loading tunnel 112 and attached to the suture 150 prior to the loading operation.

At step 201, the loader element 110, puller element 120, and the plunger element 130 are unlocked. In an embodiment, where the loading system 100 is configured as a discrete unit, the locking element 132 is released by removing the plunger element 130 from the puller element 120 and the loader element 110. Alternatively, the loader element 110 and the puller element 120 may be locked or secured through other means, and it is contemplated that during step 201 that such lock means is released thus enabling the loader element 110 and the puller element 120 to be separated.

At step 202, the implantable device 140 is pulled through the loading region 112a of the loading tunnel thereby causing the implantable device 140 to transition from an expanded state to a compressed state. The puller element 120 is pulled or moved away from the loader element 110. As the puller element 120 is moved away from the loader element 110, the suture 150 attached to the implantable device 160 and the puller element 120 pulls the implantable device 140 through the loading region 112a towards the container region 112b of the loading tunnel 112. As this happens, the funnel shape of the loading region 112a causes the implantable device 140 to be gradually compressed such that the diameter of the implantable device 140 is gradually reduced as the implantable device 140 moves toward and into the container region 112b. In one embodiment, the walls of the loading tunnel 112 provide an equally balanced compressive force around the entire circumference of the implantable device 140 as the implantable device moves through the loading tunnel 112. This reduces the likelihood of deforming the implantable device 140 during compression. Concurrent to the pulling of the implantable device 140, the rotator which is removably attached to the suture 150 is configured to move or slide away from the loader device 110 along the rotator track disposed on the loader device 110.

At step 203, and as seen in FIG. 4A, the puller element 120 is sufficiently pulled or moved away from the loader element 110 causing the implantable device 140 to be pulled into the container region 112b of the loading tunnel 112. Furthermore, the movement of the puller element 110 in conjunction with the resulting suture tension causes the rotator to move sufficiently away from the loader element 110 such that that the rotator exits the track. Thereafter, the suture tension due to the continued pulling of the puller element 120 causes the rotator 122 to rotate along the pin. The rotation of rotator 122 causes the rotator 122 to transition from a first position (while rotator was inside the rotator track) to a second position (after the rotator exists the rotator track) and/or causes the orientation of the rotator tines to change. The rotation and/or the subsequent transition of the rotator 122 cause the suture 150 that was attached to the rotator 122 to detach from the rotator 122. For example, the portion of the suture 150 that was attached to the rotator 122 between the first and second tines 122a and 122b may slide off due to the rotation thus detaching the suture 150 from the rotator 122.

At step 204, the puller element 120 is further pulled or moved away from the loader element 110 causing a complete separation of the puller element 120 and the loader element. The suture 150 is attached to the puller element 120 while it is detached from the implantable device 140. Specifically, after the detachment of the suture 150 from the rotator 122, the suture 150 is drawn through and exits the implantable device 140 and thereby detaching the suture 150 from the implantable device 140.

At step 205, and as seen in FIG. 4B, a portion of the delivery catheter 160 is placed into the loader element 110, such that the portion of the delivery catheter 160 is inserted into and/or aligned with the catheter region 112c of the loading tunnel 112. Optionally, prior to placing the delivery catheter 160 into the loader element 110, the loader tunnel 112 is first pushed towards the rear opening 110a and thereby compressing the tension element 113. Thereafter, a portion of the delivery catheter 160 is placed into the loader element 110 as described above and the loading tunnel 112 is released. The compressed tension element 113 thereby applies a force that pushes the loading tunnel 112 towards the front opening 110b; this force may be advantageous since it may ease the alignment of the delivery catheter 160 with the catheter region 112c of the loading tunnel 112 by pushing the loading tunnel 112 towards the delivery catheter 160.

At step 206, and as seen in FIG. 4C, after the portion of the delivery catheter 160 is placed into and/or substantially aligned with the loader element 110, the plunger element 130 is used to push the implantable device 140 into the delivery catheter 160. In one embodiment, the elongated portion 131 of the plunger element 130 is inserted into the loading tunnel 112 through the rear opening 110b of the loader element 110, thereafter, the elongated portion 131 forces the implantable device 140 that resides in the container region of the loading tunnel 112 into the delivery catheter 160. Thereafter, the delivery catheter containing the implantable device is removed from the loader element 110.

An alternative embodiment of a loading system is shown in FIGS. 5A and 5B. As seen FIG. 5A, an embodiment of a loading system 300 comprises a loader element 310, a puller element 320, and a plunger element (not shown). The loader element 310 comprises a front opening 310a and a rear opening 310b. The loader element 310 further comprises a loading tunnel 311 that is held in place or suspended within the housing element 310 by a tunnel mount 312. The loading tunnel 311 may comprise a loading region, a container region, and the catheter region similar to the configuration as described above. An optional first tension element 313 is disposed within the housing element 310 that applies a tension to the loading tunnel 311 and/or the tunnel mount 312.

As seen in FIGS. 5A and 5B, in one embodiment, a catheter locking element 340 comprises a first opening 341 and a second opening 342 is movably disposed within the loader element 310. The area of the first opening 341 is configured to accommodate a delivery catheter 350 while facilitates in placing and/or securing the delivery catheter 350 such that the catheter is substantially aligned with the loading tunnel 312. The second opening 342 is configured with a larger area than the first opening 341 to facilitate the insertion and/or removal of the delivery catheter 350 from the loader element 310. The first opening 341 and the second opening 342 are connected via a channel, wherein the channel is configured to accommodate the delivery catheter 350 such that the delivery catheter 350 may transition from the first opening 341 to the second opening 342 and vice-versa. In one embodiment, the catheter locking element 340 is disposed on top of a second tension element 314 within the housing element 310.

Prior to the loading operation, as seen in FIG. 5A, the second tension element 314 is compressed by the catheter locking element 340 by using a locking pin 315 that protrudes from the tunnel mount 312. The locking pin 315 may be inserted into the first opening 341 of the catheter locking element 320 thereby causing the catheter locking element 340 to compress the second tension element 314 and substantially aligns the second opening 342 with the loading tunnel 311.

The puller element 320 comprises a pin 321 and a moveable rotator 322 that is configured to rotate along the pin 321. As seen in FIG. 2B, in one embodiment, the rotator 322 comprises a body that is configured to connect to the pin 321 and a tine 322a. Alternatively, the rotator 322 may assume various other configurations such as the rotator previously described comprising multiple tines.

Additionally, the loading system 300 further comprises a suture that is affixed to a suture attachment element (not shown) on the puller element 320. The suture may be configured as a suture loop that is threaded through an implantable device 330 and removably attached to the rotator 322 as described above.

In an exemplary operation of the loading device 300, the puller element 320 is pulled or moved away from the housing element 310 until the rotator 322 rotates to release the suture and consequently the suture is released from the implantable device 330. Thereafter, a delivery catheter 350 is inserted into the loader element 310 through the second opening 342 of the catheter locking element 340. Tension is then applied to the catheter 350 which causes the tunnel mount 312 to move towards the rear opening 310b of the loader element 310. The movement of the tunnel mount 312 causes the locking pin 315 to exit from the first opening 341 of the catheter locking element 340 thereby causing the second tension element 314 to transition from a compressed state to a relaxed state which moves the catheter locking element 340 away from the base of the second tension element 314. The movement causes the first opening 341 of the catheter locking element 340 to align with the loading tunnel 311 and causes the delivery catheter 350 to exit the second opening 342 and transition through the channel into the first opening 341 as seen in FIG. 5B. Since the first opening 341 is configured with a smaller diameter than the second opening 342, by aligning with the loading tunnel 311 and placing the catheter 350 in the first opening 341, the catheter locking element 350 is configured to facilitate or aid in the stabilizing and/or the aligning of the catheter 350 with the loading tunnel 311. Thereafter, the plunger element (not shown) is applied to push the implantable device 330 into the catheter 350.

Thereafter, the plunger element is removed from the loader element 310, and the catheter 350 is release from the catheter locking element 340 by applying tension to the second tension element 314 such that the catheter 350 transitions back into the second opening 342, thereafter, the catheter 350 is removed from the loader element 310.

Figure 6C:
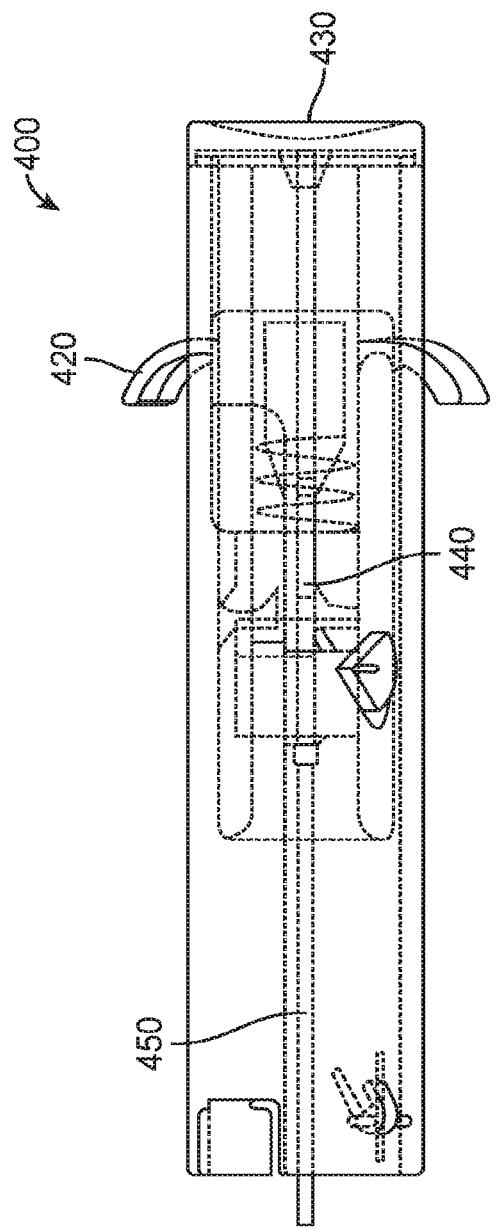

In yet another embodiment, as seen in FIGS. 6A-C, one embodiment of a loading system 400 comprises a loader element 410, puller element 420, and the plunger element 430. The loader element 410 comprises loading tunnel 411 comprising a loading region, container region, and a catheter region as described above. In one embodiment, the loader element 410 further comprises a tunnel mount 412, a pin connected to the loader element 410 and a rotator 413 configured to rotate along the pin. A suture is affixed to the puller element and it is removably attached to implantable device 440 and the rotator 413 as described above. The loader element 410 further comprises a tension element 414 that is disposed between tunnel mount 412 and the loading portion of the loading tunnel 411a. The puller element 420 comprises a tunnel locking element 421 that is configured to secure the loading tunnel 411 when the puller element 420 and the loader element 410 are mated.

In an exemplary operation of the loading system 400, as seen in FIG. 6B the loading element 410 and the plunger element 430 are initially mated. Likewise, the puller element 420 and the loader element 410 are initially connected. As seen in FIG. 6C, a delivery catheter is first placed into the loading system 400 through the puller element 420. The puller element 420 is moved towards the plunger element 430, and consequently, a tension is applied through the suture to pull the implantable device 440 from the loading portion into the housing portion of the loading tunnel 411. Further movement of the puller element 420 causes the rotator 413 disposed on the loader element 410 to rotate and the suture is released from the rotator 413. Thereafter, the suture is released from the implantable device 440. Further movement of the puller element 420 towards plunger element 430 causes the elongated portion of the plunger element 430 to push the implantable device 440 into the delivery catheter 450, thereafter, the loaded delivery catheter is removed from the loader element 410.

Also provided are kits for use in practicing the subject methods, where the kits typically include one or more of the above system for loading an implantable device, as described above. In certain embodiments, the kits at least include a loader element. Kits may also include a plunger element, an implantable device, and/or a delivery catheter. Additional components may be included in the kit.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate While the above is a complete description of various embodiments, any of a number of alternatives, modifications, and equivalents may be used in alternative embodiments. Therefore, the above description should not be taken as limiting the scope of the invention as it is defined by the appended claims.

What is claimed is:

1. A system for loading an implantable pulmonary device into a container, comprising:
   a loading element comprising a loading tunnel configured to contract an implantable pulmonary device into a compressed state of reduced size relative to an expanded state as the implantable pulmonary device travels through the loading tunnel;
   a puller element that is removably attached to the implantable pulmonary device, wherein the puller element pulls the implantable pulmonary device through the loading tunnel; and
   a plunger element, wherein the plunger element comprises an elongated portion that is configured to push the implantable pulmonary device through the loading tunnel;
   wherein the puller element automatically releases the implantable pulmonary device after the implantable pulmonary device contracts into the compressed state.

2. The system of claim 1, wherein the plunger element is configured to push the implantable pulmonary device into a delivery catheter.

3. A system for loading an implantable pulmonary device into a container, comprising:
   a loading element comprising a loading tunnel configured to contract an implantable pulmonary device into a compressed state of reduced size relative to an expanded state as the implantable pulmonary device travels through the loading tunnel; and
   a puller element that is removably attached to the implantable pulmonary device, wherein the puller element pulls the implantable pulmonary device through the loading tunnel;
   wherein the puller element automatically releases the implantable pulmonary device after the implantable pulmonary device contracts into the compressed state;
   wherein the loading tunnel further defines an internal transfer cavity that communicates with the loading cavity, the transfer cavity sized to receive the implantable device from the loading cavity and retain the implantable pulmonary device in the compressed state; and
   wherein the loading tunnel further defines a container cavity that communicates with the transfer cavity, the container cavity sized to receive a container that receives the implantable pulmonary device in the compressed state.

4. A system for loading an implantable pulmonary device into a container, comprising:
   a loading element comprising a loading tunnel configured to contract an implantable pulmonary device into a compressed state of reduced size relative to an expanded state as the implantable pulmonary device travels through the loading tunnel; and
   a puller element that is removably attached to the implantable pulmonary device, wherein the puller element pulls the implantable pulmonary device through the loading tunnel;
   wherein the puller element automatically releases the implantable pulmonary device after the implantable pulmonary device contracts into the compressed state; and
   wherein the container is a delivery catheter that is configured to deliver the implantable pulmonary device to a lung region.

5. A system for loading an implantable pulmonary device into a container, comprising:
- a loading element comprising a loading tunnel configured to contract an implantable pulmonary device into a compressed state of reduced size relative to an expanded state as the implantable pulmonary device travels through the loading tunnel;
- a puller element that is removably attached to the implantable pulmonary device, wherein the puller element pulls the implantable pulmonary device through the loading tunnel; and
- a tension element that is configured to communicate a force to the loading tunnel;
- wherein the puller element automatically releases the implantable pulmonary device after the implantable pulmonary device contracts into the compressed state.

6. A system for loading an implantable pulmonary device into a container, comprising:
- a loading element comprising a loading tunnel configured to contract an implantable pulmonary device into a compressed state of reduced size relative to an expanded state as the implantable pulmonary device travels through the loading tunnel;
- a puller element that is removably attached to the implantable pulmonary device, wherein the puller element pulls the implantable pulmonary device through the loading tunnel; and
- a container locking element that is configured to secure and align the container with the loading element;
- wherein the puller element automatically releases the implantable pulmonary device after the implantable pulmonary device contracts into the compressed state.

7. A system for loading an implantable pulmonary device into a container, comprising:
- a loading element comprising a loading tunnel configured to contract an implantable pulmonary device into a compressed state of reduced size relative to an expanded state as the implantable pulmonary device travels through the loading tunnel; and
- a puller element that is removably attached to the implantable pulmonary device, wherein the puller element pulls the implantable pulmonary device through the loading tunnel;
- wherein the puller element automatically releases the implantable pulmonary device after the implantable pulmonary device contracts into the compressed state; and
- wherein a rotator disposed on the puller element is removably attached to a suture; and rotation of the rotator causes the suture to detach from the rotator thereby releasing the implantable pulmonary device from the puller element.

8. The system of claim 7, wherein the suture is drawn through and exits the implantable pulmonary device after the detachment of the suture from the rotator thereby detaching the suture from the implantable pulmonary device.

9. A system for loading an implantable pulmonary device into a container, comprising:
- a loading element comprising a loading tunnel configured to contract an implantable pulmonary device into a compressed state of reduced size relative to an expanded state as the implantable pulmonary device travels through the loading tunnel; and
- a puller element that is removably attached to the implantable pulmonary device, wherein the puller element pulls the implantable pulmonary device through the loading tunnel;
- wherein the puller element automatically releases the implantable pulmonary device after the implantable pulmonary device contracts into the compressed state; and
- wherein the puller element comprises a pin and a rotator that is configured to rotate along the pin.

10. The system of claim 9, wherein the rotator comprises a body that is configured to connect to the pin, a first tine and a second tine, wherein the first tine is longer than the second tine.

11. The system of claim 9, wherein the loading element further comprises a rotator track that is configured to accommodate the rotator.

12. The system of claim 11, wherein the rotator is configured to be received by the rotator track such that the rotator resides within the rotator track when the loader element and the puller element are connected.

13. The system of claim 12, wherein the rotator track is further configured to allow the rotator to slide along the rotator track when the puller element is moved away from the loader element.

* * * * *